United States Patent [19]

Dosaj et al.

[11] Patent Number: 4,898,960

[45] Date of Patent: Feb. 6, 1990

[54] METHOD OF DIRECT PROCESS PERFORMANCE IMPROVEMENT VIA CONTROL OF SILICON MANUFACTURE

[75] Inventors: Vishu D. Dosaj, Midland, Mich.; Roland L. Halm, Madison, Ind.; Oliver K. Wilding, Jr., Wales, United Kingdom

[73] Assignee: Dow Corning Corporation, Midland, Mich.

[21] Appl. No.: 945,128

[22] Filed: Dec. 22, 1986

[51] Int. Cl.$^4$ ............................ C07F 7/08; C07F 7/16
[52] U.S. Cl. .................................................... 556/472
[58] Field of Search ........................................ 556/472

[56] References Cited

U.S. PATENT DOCUMENTS 4,602,101  7/1986  Halm et al. ........................ 556/472

Primary Examiner—Paul F. Shaver
Attorney, Agent, or Firm—Carl A. Yorimoto; James E. Bittell

[57] ABSTRACT

What is disclosed is a method of improving the performance of the direct process for preparing alkylhalosilanes using an alkylhalide and silicon. The method is based on the control of the phosphorous that enters the silicon used in the direct process, by controlling the amount of phosphorous that enters the silicon during the manufacture of the silicon itself.

32 Claims, No Drawings

METHOD OF DIRECT PROCESS PERFORMANCE IMPROVEMENT VIA CONTROL OF SILICON MANUFACTURE

SUMMARY OF THE INVENTION

This invention deals with the control of phosphorous through selection of raw materials or the addition of phosphorous containing compounds in the production of silicon used in the direct process to produce alkylhalosilanes. The phosphorous, in the reduced state, acts as a promoter in the direct process when used in certain quantities. Silicon containing the phosphorous can be used in the direct process when the level of phosphorous is controlled in the silicon as it is being produced.

BACKGROUND OF THE INVENTION

This invention deals with a method of improving the performance of a process for the manufacture of alkylhalosilanes. This invention deals mainly with the production of silicon, which is used in the direct process for the production of alkylhalosilanes. More particularly, this invention deals with a method of controlling the level of phosphorous promoters in silicon used in the direct process, in order that the direct process in which the treated silicon is used is enhanced in terms of reactivity and selectivity of the direct process reactions.

The benefits to be derived by the use of this invention are increased alkylhalosilane yields, selectivity of certain alkylhalosilanes over other, less preferred, alkylhalosilanes and, overall high utilization of raw materials used in the direct process reaction mixture.

The direct process for producing alkylhalosilanes is well-known and has been refined and modified in many ways since Rochow first set forth the manner in which one could obtain alkylhalosilanes by contacting alkylhalides with silicon at elevated temperatures. In U.S. Pat. No. 4,602,101, issued July 22, 1986, in the name of Roland L. Halm, Oliver K. Wilding, Jr. and Regie H. Zapp, there is disclosed the use of certain phosphorous compounds in the direct process in the presence of silicon, copper and tin, to enhance the reactivity and selectivity of the reaction to produce alkylchlorosilanes. Such phosphorous compounds are selected from elemental phosphorous, metal phosphides and phosphorous compounds capable of forming metal phosphides in the reaction mass of the direct process.

Early investigators dealt with the problems of enhancing the reactivity and selectivity of the direct process by approaching the problems from the standpoint of the physical forms of the raw materials; the treatment of the surfaces of the raw materials or the inclusion of components other than silicon and copper in the reactor feed. Thus. Nitzsche, in U.S. Pat. No. 2,666,776 issued Jan. 16, 1954, teaches that alloys of silicon and copper which also contain metals from the 5th to the 8th groups of the periodic table such as, for example, cobalt, nickel, iron or phosphorous increase the efficiency of the process if an activator, for example, a copper salt is also used.

Zoch, in U.S. Pat. No. 3,446,829, issued May 27, 1969, teaches a contact mass for the direct process containing silicon, a copper or silver catalyst and a cadmium promoter. This combination can be used as a powder mix or an alloy.

Rossmy, in German ALS No. 1,165,026 teaches doping of silicon by sintering powdered silicon or ferrosilicon with powdered copper alloys containing certain additives. Such additives have been described as antimony, indium, thallium, gallium, phosphorous, arsenic and bismuth. Also, in Soviet Inventions Illustrated, General Organic Section, February 1966, page 2, there is essentially described the Rossmy teaching wherein antimony and phosphorous are used in combination as an alloy, with silicon and copper, And finally, in an article entitled "Influence of Additions of Some Elements to Silicon-Copper Alloys on Their Activity in the Reaction with Methyl Chloride," Lobusevich, N. P. et al., translated from Zhurnal Obshchei Khimii, Vol. 34, No. 8, pp 2706-2708, August, 1964, silicon-copper alloys are described in which certain additives are used in conjunction therewith to enhance the direct process. The article shows phosphorous to be a catalytic poison at concentrations of 50 to 80 ppm based on the alloy. Further, it is noted in the summary that phosphorous when added to alloys in addition to promoters, considerably improves the catalytic property of the silicon-copper alloys. It fails, however, to suggest which promoters will or will not improve this property.

Thus, collectively, the prior art teaches that combinations of silicon-copper alloys and certain other materials can be used to affect the reactivity or selectivity of the direct process. These combinations can take the form of alloys or mixed powders, or the like, and can be used directly in the process. All of the prior art teaches alloys i.e. the melting together of certain components, but the prior art does not teach the production of silicon for the direct process wherein the level of phosphorous in the silicon is controlled such that known amounts of phosphorous are introduced to the direct process reactor with the result of enhanced reactivity and selectivity.

In the instant invention, it was found that the phosphorous, which has the beneficial effect on the direct process, can be introduced into the silicon at the levels required for the direct process, by controlling the amount of phosphorous that enters the silicon during the smelting of the silicon. It has been discovered that certain quartz deposits contain phosphorous which survives the smelting process. In addition, certain phosphorous compounds can be added to the raw materials that go into the silicon smelting in order to obtain phosphorous in the final silicon product. Further, it has been discovered that phosphorous is also a contaminant in the raw materials that are used during the smelting of silicon, such as, for example, the carbonaceous reductants used in the smelting process.

Thus, the instant invention deals with a method of improving the performance of a process for the manufacture of alkylhalosilanes, said process comprising, contacting an alkylhalide with silicon, at a temperature of 250° to 350° C., in the presence of tin or tin compounds, and copper or copper compounds, wherein there is at least also present, 25 to 2500 parts per million, based on the silicon in the reaction mass, of a phosphorous promoter, which method comprises controlling the level of the phosphorous promoter in the silicon by incorporating and controlling the level of phosphorous in the mass of the silicon, by controlling the amount of phosphorous that is introduced into the silicon during the manufacture of the silicon.

The silicon manufactured in this manner has been found to contribute to enhanced reactivity and selectivity in the direct process for the production of alkylhalosilanes.

THE INVENTION

What is disclosed herein as the invention therefore is a method of improving the performance of a process for the manufacture of alkylhalosilanes, said process comprising, contacting an alkylhalide with silicon, at a temperature of 250° to 350° C., in the presence of tin or tin compounds, and copper or copper compounds, wherein there is at least also present, 25 to 2500 parts per million based on the silicon in the reaction mass, of a phosphorous promoter, which method comprises controlling the level of the phosphorous promoter in the silicon by incorporating and controlling the level of phosphorous in the mass of silicon, by controlling the amount of phosphorous that is introduced into the silicon from the raw materials used in the manufacturing of the silicon.

Also disclosed is a composition which is the silicon produced by the inventive method disclosed herein, The key to the invention is the control of the amount of phosphorous that is actually added to the silicon arc furnace as the silicon is being made. It is known that certain quartz minerals contain phosphorous while others do not. Thus, the amount of phosphorous in the silicon can be controlled by blending certain quartz types to arrive at the proper amount of phosphorous in the silicon of this invention. It is also known that there are phosphorous contaminants in the other raw materials used in the manufacturing of silicon. For example, it is known that the carbonaceous reductants used as raw materials in the manufacturing of silicon contain phosphorous. Thus, one can use reductants that contain known amounts of phosphorous with reductants that do not contain phosphorous and blend these reductants in much the same manner that the quartz deposits are blended to give the requisite amount of phosphorous in the smelted silicon. Further, it is known that the bark of most trees contain an order of magnitude higher impurities than the wood itself, so that one could use appropriate blends of bark with wood chips as part of a reductant in order to obtain reductants rich in phosphorous. The only other major impurity in wood bark is calcium, which can be refined by oxygen refining to attain the desired levels in the silicon. Also, one can balance the quartz minerals with the proper reductants in order to obtain a silicon which has the requisite amount of phosphorous. In addition, there are certain non-volatile phosphorous compounds that can be added directly to the silicon arc furnace in order to obtain silicon with the requisite amount of phosphorous. For those skilled in the art, it is therefore evident that there are a number of means by which the phosphorous can be introduced to the silicon furnace and there are numerous ways in which one skilled in the art can control the amount of phosphorous that is introduced to the silicon furnace in order to obtain a silicon that has a controlled amount of phosphorous in it.

As will be recognized by those skilled in the art, it is essential that the amount of phosphorous in the raw materials be known so that the balancing and therefore the control of the amount of phosphorous in the eventual product can be controlled. Thereafter, it is a simple matter of introducing the proper amount of each reactant, or reactant and phosphorous compound, to achieve the desired level of phosphorous in the silicon.

Some phosphorous compounds found useful in this invention are tricalcium phosphate and the phosphides, such as, for example, aluminum phosphide, calcium phosphide, copper phosphide and iron phosphide.

Silicon produced by the inventive method herein is produced by the same essential means by which silicon and silicon-ferro alloys are being produced commercially with the exception of the use of the phosphorous compounds during the smelting of the silicon. In the method of this invention, the key element is the control of the amount of phosphorous that goes into the silicon reduction process so that the resulting silicon will have the proper amounts of phosphorous available for the direct process. The direct process, as it is disclosed and set forth in the U.S. Pat. No. 4,602,101 issued July 22, 1986, is incorporated herein by reference for what it teaches about the direct process and the catalysis thereof.

Silicon is typically produced in a submerged electric arc furnace via carbothermic reduction of silicon dioxide ($SiO_2$) with a solid carbonaceous reducing agent. The silicon dioxide may be in the form of quartz, sand, fused or fume silica or the like. The carbonaceous material may be in the form of coke, coal, wood chips, and other forms of carbon containing materials. The feeding of the solid reactants into the silicon furnace can be effected by conventional means such as gravity feed or gas pressure in combination with a gas-lock valve, screw feeders, pneumatic conveyors, and the like. The silicon dioxide and reducing agent may be fed alternately, first as a mixture of silicon dioxide and the reducing agent, and then as silicon dioxide by itself, or the reactants can all be fed simultaneously. The phosphorous compounds useful in this invention can be added to the furnace in this same manner. The form of the silicon dioxide used in the method for producing silicon can take the form of powders, granules, lumps, pebbles, pellets and briquettes and the reducing agent takes the form of powders, granules, chips, lumps, pellets, and briquettes. Thus, the phosphorous compounds and the solid reactants are smelted under conventional processing means to obtain silicon. Such silicon can thereafter be refined without deleterious effect o the phosphorous in the silicon.

Recovery of the molten silicon for refining can be handled by any conventional means for removal of the silicon from the reaction zone of the furnace such as by batch or continuous tapping.

The success of the silicon process is measured by the retention of phosphorous in the silicon and the effect of such silicon when used in the direct process. Enhanced activity is measured by the weight percent of $(CH_3)_2SiCl_2$ that is obtained; the ratio of $CH_3SiCl_3$ to $(CH_3)_2SiCl_2$ and the percent silicon converted to useful products, expressed in these examples as $Me_2$ weight percent. $Me/Me_2$ ratio and Si conversion (Weight %), respectively. A high $Me_2$ weight percent; low $Me/Me_2$ ratio and a high Si conversion all indicate excellent activity of the treated silicon.

The direct process tests were carried out mostly on laboratory scale runs with some data obtained on large scale equipment.

The examples are provided to illustrate the detailed points of the invention and they should not be construed as limiting the invention as it is set forth in the appended claims.

The direct process reactor used for these examples is similar to that described in Maas et al., U.S. Pat. No. 4,218,387 and is familiar to those skilled in the art for producing methylchlorosilanes using silicon and methylchloride. In general, the reaction is carried out by passing the methyl chloride, in vapor or gas form, over the surface of the silicon charge while maintaining the silicon charge at an elevated temperature. The heating of the reactant mixture is carried out, in this case, by immersing the reactor in a sand bath as a heat transfer medium.

The products of the reaction and any unreacted materials are condensed and collected in cold traps immersed in dry ice and alcohol. The products and unreacted materials are evaluated by gas chromatography by pouring the collected materials into cooled bottles (dry ice/isopropanol), cooling the chromatograph syringes and injecting samples into the gas chromatograph as quickly as possible.

The charge for the direct process reactor is prepared by grinding silicon and shaking the ground silicon in a bottle for two or three minutes with any other solid ingredients desired to be included in the reaction. The charge is placed in the reactor and the reactor is closed and weighed to give initial charge weights. The gas flow for fluidization is started. The reactor is immersed in the sand bath. The receivers for the effluent are also weighed and then connected by tubes to the reactor. The reactor is heated by the sand bath and the bath is continuously fluidized to maintain close tolerances on the temperature.

The receiver (cold traps) are placed in the dry ice baths. After a few minutes the methylchloride flow to the reactor is started. After certain periods of time, generally 44 hours, and varying temperatures ranging from 250° C. to 350° C., the methylchloride flow is terminated, and the receivers are disconnected and weighed prior to analysis. The reactor is removed from the sand bath after cooling and it is also weighed. This procedure is used essentially as described, throughout the examples herein.

For purposes of interpreting these examples and evaluating the results, the following apply:

$$\text{Me/Me}_2 \text{ ratio} = \frac{\text{Weight \% CH}_3\text{SiCl}_3}{\text{Weight \% (CH}_3)_2\text{SiCl}_2}$$

$$\% \text{ Si conversion} = 100\% \times \frac{\text{amount silicon left in the charge}}{\text{Total amount of silicon charged}}$$

Also in the following examples, the silicon was processed in a submerged arc furnace using conventional raw materials that are used in the industry with or without the various phosphorous additives. In order to evaluate the level of phosphorous in the smelted silicon, one has to understand how to assess the amount of phosphorous that is being added to the silicon reactor by way of the raw materials.

In this example, the inventors have tried to show the influence of the phosphorous in the feed as it goes to the silicon furnace. In the table below, item A shows the average silicon performance in the Direct Process for 48 runs where Calcium phosphate, as a natural part of the quartz feeds was added to the arc furnace during the preparation of the silicon. Item B shows the average silicon performance in the Direct Process for control runs where quartz feed to the furnace was used which contained no natural calcium phosphate, and where no calcium phosphate was added. Phosphorous content of the silicon for the runs in B were less than 30 ppm. Item C shows the average of eleven runs where the silicon was produced after resuming silicon production wherein quartz, containing calcium phosphate, was added as a feed to the silicon furnace. All of the silicon was oxygen refined.

| ITEM | $\text{Me}_2\text{SiCl}_2$ Avg. Wt. % | $\text{Me/SiCl}_3$ Avg. Wt. % | % Silicon Conversion Average |
|---|---|---|---|
| A | 89.7 | 5.0 | 65.4 |
| B | 84.1 | 7.5 | 55.0 |
| C | 89.0 | 5.3 | 66.1 |

Note how the performance fell off on item B when the quartz without phosphorous was used as the feed in the arc furnace, and how the good performance resumed when the use of quartz containing phosphorous was resumed.

Thus, for purposes of this invention, the following impurity balance calculations were used to arrive at the distribution coefficient of the phosphorous in the smelted silicon and the phosphorous that was lost to the gaseous effluent.

IMPURITY BALANCE

Input (where I = impurity)
Weight of $\text{SiO}_2$ × Weight percent I in $\text{SiO}_2$
Weight of coal × Weight percent I in coal
Weight of coke × Weight percent I in coke
Weight of wood × Weight percent I in wood $$\frac{\text{Weight electrode}}{\text{Unit weight silicon}} \times \text{Weight SiO}_2 \times \frac{28}{60} \times$$

Si recovery × Weight percent I in the electrode.

Output

Weight $\text{SiO}_2 \times \frac{28}{60} \times$ Si recovery × Weight % I in Silicon Input × Distribution coefficient = OUTPUT Thus, for these examples:

| RAW MATERIAL | Weight lbs | ppm P |
|---|---|---|
| #1 quartz | 351 | 210 |
| #2 quartz | 699 | 15 |
| Coke | 93 | 1 |
| Coal | 408 | 8 |
| Wood | 576 | 2 |
| Electrode | 250/ton Si | 1 |

The calculations are: (Wt. #1 × Wt. % P + Wt. #2 × Wt % P + Wt. coke × Wt. % P + Wt. coal × Wt. % P + Wt. wood × Wt. % P + Wt. elec × Wt. % P) × Dist. Coeff. = Wt.

$\text{SiO}_2 \times \frac{28}{60} \times$ (silicon Rec.) × Wt. % P in Si, where the Dist. Coeff. is the distribution coefficient.

The Distribution Coefficient of P = the distribution of P between silicon and the gaseous effluent.

79×Dist. Coeff.=490×(Si rec.)×Wt. % P  Equation (I)

Equation (I) allows one to predict the amount of phosphorous that will be found in smelted and refined silicon based on the percentage silicon recovery. The distribution coefficient for phosphorous was determined by analyzing all the input raw materials to the furnace, as well as the silicon produced and the gaseous effluents collected in the form of fume. Based on the overall material balance with conventional raw materials a distribution coefficient of 0.14 was obtained. In the example, in Table 1, using quartz containing higher levels of phosphorous, the distribution coefficient calculated from known analysis of materials was measured at 0.10.

Table I calculated phosphorous levels in silicon compare favorably to the samples analyzed from the silicon produced using the analysis of the materials in Table II.

TABLE I

| Distribution Coefficient | Silicon Recovery Wt. % | ppm P |
|---|---|---|
| 0.10 | 90 | 180 |
|  | 85 | 190 |
|  | 80 | 200 |
|  | 75 | 210 |

Using the calculations above and the knowns, four runs were made in the silicon arc furnace to give silicon that contained phosphorous. The runs were designated A,B,C and D. The results of the silicon smelting runs can be found in Table II while the runs in the direct process, using A, B, C and D had the results shown in Table III.

TABLE II

|  | Tap Analysis ppm P | Pre ground Analysis Sample ppm P |
|---|---|---|
| A | 100 | 150 |
| B | 110 | 110 |
| C | 140 | 120 |
| D | 170 | 100 |

In this example, "tap analysis" means an analysis of a sample taken directly from the tapped silicon in the molten state directly after it was removed from the furnace. "Pre ground analysis" means an analysis of the silicon after it was cooled and ground, just prior to its use in the direct process. All silicon was refined using conventional oxygen refining.

TABLE III

| Sample | Me Wt. % | Me$_2$ Wt. % | Me/Me$_2$ Ratio | % Si Conversion |
|---|---|---|---|---|
| A | 4.05 | 91.66 | .044 | 44.27 |
| *A | 5.23 | 90.26 | .058 | 50.00 |
| B | 3.95 | 91.88 | .043 | 77.08 |
| *B | 4.32 | 91.35 | .047 | 85.94 |
| C | 4.14 | 92.07 | .045 | 72.66 |
| *C | 4.01 | 92.27 | .043 | 85.42 |
| D | 4.46 | 90.56 | .049 | 73.18 |
| *D | 4.35 | 91.17 | .048 | 61.72 |

*duplicate runs

Similar results are obtained when charcoal is used as the source of phosphorous in the raw material mix. The amount of phosphorous in charcoal ranges from about 0.035 to 0.15 weight percent.

Thus, when using charcoal containing 0.1 weight % phosphorous, as the reductant, and other conventional raw materials, one can expect about 180 ppm of phosphorous in the resulting silicon, wherein the distribution coefficient is about 0.14 and the silicon recovery is about 85%.

When phosphorous compounds are added to the raw material mix, for example, $Ca_3(PO_4)_2$, about 0.02 weight percent of tricalcium phosphate is added based on the weight of $SiO_2$. This gives about 150 ppm of phosphorous in the resulting silicon, wherein there is a distribution coefficient of about 0.1 and a silicon recovery of about 85%.

It has been discovered that rice hulls also contain enough phosphorous to allow them to be used as a raw material source in the silicon furnace within the scope of this invention. Rice hulls when added as a raw material to the silicon furnace, convert to SiC upon heating. This SiC is useful as a feed material to make silicon and thus carries with it, phosphorous, which is carried through to the final silicon product.

Thus, it can be seen that the control of the phosphorous in the raw material mix to a silicon furnace, controls the amount of phosphorous in the resulting silicon, and that such a phosphorous-containing silicon can be used in the direct process to enhance the reactivity and selectivity thereof. The phosphorous not only survives the rigors of the smelting process, but survives in the form that is useful in the direct process.

That which is claimed is:

1. A method of improving the performance of a process for the manufacture of alkylhalosilane, said process comprising, contacting an alkylhalide with silicon at a temperature of 250° to 350° C. in the presence of tin or tin compounds, and copper or copper compounds, wherein there is at least also present 25 to 2500 parts per million, based upon the silicon in a reaction mass, of a phosphorous promoter, which method further comprises controlling the level of the phosphorous promoter in the silicon by incorporating and controlling the level of phosphorous in the mass of the silicon by controlling the amount of phosphorous that is introduced into a silicon smelter during the manufacture of silicon.

2. A method as claimed in claim 1, wherein the phosphorous is incorporated into the silicon by using phosphorous-containing quartz as a raw material.

3. A method as claimed in claim 1, wherein the phosphorous is incorporated into the silicon by using phosphorous-containing coal as a raw material.

4. A method as claimed in claim 1, wherein the phosphorous is incorporated into the silicon by using phosphorous-containing coke as a raw material.

5. A method as claimed in claim 1, wherein the phosphorous is incorporated into the silicon by using phosphorous-containing charcoal as a raw material.

6. A method as claimed in claim 1, wherein the phosphorous is incorporated into the silicon by using rice hulls as a raw material.

7. A method as claimed in claim 1, wherein the phosphorous is incorporated into the silicon by using a phosphorous compound as a raw material.

8. A method as claimed in claim 1, wherein the phosphorous is incorporated into the silicon by using a mixture of phosphorous-containing raw materials.

9. A method as claimed in claim 1, wherein the phosphorous is incorporated into the silicon by using a mixture of phosphorous-containing and nonphosphorous-containing raw materials.

10. A method as claimed in claim 1, wherein the silicon produced contains 25 to 2500 parts per million of phosphorous as tapped from the silicon smelter.

11. A method as claimed in claim 1, wherein the phosphorous that is introduced into the silicon smelter is in the form of tricalcium phosphate.

12. A method as claimed in claim 1, wherein the phosphorous that is introduced into the silicon smelter is in the form of a nonvolatile phosphide.

13. A method as claimed in claim 12, wherein the phosphide is aluminum phosphide.

14. A method as claimed in claim 12, wherein the phosphide is calcium phosphide.

15. A method as claimed in claim 12, wherein the phosphide is copper phosphide.

16. A method as claimed in claim 12, wherein the phosphide is iron phosphide.

17. A method of improving the performance of a process for the manufacture of alkylhalosilane, said process comprising, contacting an alkylhalide with silicon at a temperature of 250° to 350° C. in the presence of tin or tin compounds, zinc or zinc compounds, and copper and copper compounds, wherein there is at least also present 25 to 2500 parts per million, based upon the silicon in the reaction mass, of a phosphorous promoter, which method further comprises controlling the level of the phosphorous promoter in the silicon by incorporating and controlling the level of phosphorous in the mass of the silicon by controlling the amount of phosphorous that is introduced into a silicon smelter during the manufacture of silicon.

18. A method as claimed in claim 17, wherein the phosphorous is incorporated into the silicon by using phosphorous-containing quartz as a raw material.

19. A method as claimed in claim 17, wherein the phosphorous is incorporated into the silicon by using phosphorous-containing coal as a raw material.

20. A method as claimed in claim 17, wherein the phosphorous is incorporated into the silicon by using phosphorous-containing coke as a raw material.

21. A method as claimed in claim 17, wherein the phophorous is incorporated into the silicon by using phosphorous-containing charcoal as a raw material.

22. A method as claimed in claim 17, wherein the phosphorous is incorporated into the silicon by using rice hulls as a raw material.

23. A method as claimed in claim 17, wherein the phosphorous is incorporated into the silicon by using a phosphorous compound as a raw material.

24. A method as claimed in claim 17, wherein the phosphorous is incorporated into the silicon by using a mixture of phosphorous-containing raw materials.

25. A method as claimed in claim 17, wherein the phosphorous is incorporated into the silicon by using a mixture of phosphorous-containing and nonphosphorous-containing raw materials.

26. A method as claimed in claim 17, wherein the silicon produced contains 25 to 2500 parts per million of phosphorous as tapped from the silicon smelter.

27. A method as claimed in claim 17, wherein the phosphorous that is introduced into the silicon smelter is in the form of tricalcium phosphate.

28. A method as claimed in claim 17, wherein the phosphorous that is introduced into the silicon smelter is in the form of a nonvolatile phosphide.

29. A method as claimed in claim 28, wherein the phosphide is aluminum phosphide.

30. A method as claimed in claim 28, wherein the phosphide is calcium phosphide.

31. A method as claimed in claim 28, wherein the phosphide is copper phosphide.

32. A method as claimed in claim 28, wherein the phosphide is iron phosphide.

* * * * *